(12) United States Patent
Psaros

(10) Patent No.: US 6,286,505 B1
(45) Date of Patent: Sep. 11, 2001

(54) PORTABLE ANAESTHETIC MACHINE AND EMERGENCY KIT

(75) Inventor: Georgios Psaros, Tullinge (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/179,088

(22) Filed: Oct. 27, 1998

(30) Foreign Application Priority Data

Dec. 4, 1997 (SE) .................................... 9704508

(51) Int. Cl.$^7$ ................................................ A61M 16/00
(52) U.S. Cl. .......................... 128/203.12; 128/204.18; 128/204.23; 128/912
(58) Field of Search ................. 128/203.12, 200.14, 128/200.11, 205.13, 204.23, 204.18, 204.28, 912, 203.11, 203.28, 203.21

(56) References Cited

U.S. PATENT DOCUMENTS

| | | | |
|---|---|---|---|
| 2,944,547 | * 7/1960 | Ziherl et al. | 128/203.21 |
| 3,556,097 | * 1/1971 | Wallace | 128/202.23 |
| 4,360,018 | * 11/1982 | Choksi | 128/205.12 |
| 4,446,864 | * 5/1984 | Watson et al. | 128/207.14 |
| 4,502,481 | * 3/1985 | Christian | 128/205.24 |
| 4,991,576 | * 2/1991 | Henkin et al. | 128/203.28 |
| 5,119,807 | 6/1992 | Roberts . | |
| 5,181,508 | 1/1993 | Poole, Jr. . | |
| 5,228,434 | * 7/1993 | Fishman | 128/203.12 |
| 5,277,175 | 1/1994 | Riggs et al. . | |
| 5,419,316 | * 5/1995 | Bernstein | 128/203.12 |
| 5,479,920 | * 1/1996 | Piper et al. | 128/204.23 |
| 5,503,146 | * 4/1996 | Froehlich | 128/204.23 |
| 5,988,162 | * 11/1999 | Retallick, III | 128/203.12 |

* cited by examiner

Primary Examiner—John G. Weiss
Assistant Examiner—V. Srivastava
(74) Attorney, Agent, or Firm—Schiff Hardin & Waite

(57) ABSTRACT

A portable anaesthetic machine allows dispensing of a liquid anaesthetic to a patient, which is sometimes desirable and may be hard to achieve, especially with portable equipment. This portable anaesthetic machine has a gas flow generator for generating a flow of gas at an adjustable pressure and/or flow rate, an inspiratory line and an expiratory line. The gas flow generator, inspiratory line and expiratory line constitute the gas flow pathways for the respirator. A membrane is arranged in the gas flow pathways, made of a self-sealing material. The membrane can be punctured by a syringe needle for dispensing the liquid anaesthetic into the gas flow pathways an optional number of times.

13 Claims, 1 Drawing Sheet

PORTABLE ANAESTHETIC MACHINE AND EMERGENCY KIT

BACKGROUND OF THE INVENTION

1. Field of the Invention

The present invention relates to a portable anaesthetic as well as to a portable anaesthetic.

2. Description of the Prior Art

Many different respirators are available for specific uses in the treatment of patients. Anaesthetic machines, which are generally stationary because of their size, like the KION anaesthetic machine from Siemens-Elema AB, Solna, Sweden are used to anaesthetize patients prior to surgery. Intensive care often utilizes multifunction ventilators, capable of operating in a number of modes, such as the Servo Ventilator 300, Siemens-Elema AB. Simpler ventilators are employed for sub-acute care and the care of patients in their homes. Completely portable ventilators are being developed, as described in Swedish Patent Application 9703290-8, corresponding to co-pending U.S. application Ser. No. 09/149, 023, filed Sep. 8, 1998 ("Ventilator Suitable For Miniaturization," G. Psaros) assigned to the present assignee, Siemens-Elema AB. Special emergency equipment for lifesaving and emergency treatment at accident sites is also available.

In particular, portable equipment has limitations in its ability to administer additives, in particular anaesthetics to the patient. Many substances, which could be advantageously administered via the lungs, must either be injected, with all the associated risks found at an accident site, or the medication or substance must be administered with a separate inhaler, which means that the respiratory assistance will be interrupted.

SUMMARY OF THE INVENTION

An object of the present invention is to provide a portable a portable anaesthetic to a patient connected to the machine can be performed in a safe and reliable fashion with no need to interrupt respiratory assistance.

Another object of the invention is to provide a portable anaesthetic emergency kit for inhalation anaesthesia. Such an emergency kit would be of tremendous benefit in the rapid treatment of or surgery on acutely injured patients.

The first of the above objects is achieved in accordance with the principles of the present invention in a portable anaesthetic machine having a gas flow generator for generating a flow of gas at an adjustable pressure and/or flow rate, an inspiratory line and an expiratory line, the gas flow generator, the inspiratory line and the expiratory line forming a gas flow pathway for the anesthetic machine, and a membrane disposed in the gas flow pathway and accessible from an exterior of the anesthetic machine, the membrane being made of a self-sealing material through which a specific amount of liquid anesthetic can be dispensed into the gas flow pathway a number of times.

The above reference to dispensing of the liquid anesthetic through the membrane "a number of times" means that the membrane can be successively re-used (until it wears out). Also, as used above the term "anesthetic machine" encompasses a respirator and refers to any suitable type of respirator which, in accordance with the invention, is made capable of administering anesthetic.

Membranes, which can be punctured with a syringe needle tip and then self-seal when the needle is withdrawn, are known from e.g. implantable insulin pumps. A reservoir in these insulin pumps is replenished with insulin by inserting a syringe needle through the skin of the patient, through a membrane on the implanted insulin pump and into the pump's reservoir. The contents of the syringe are then discharged, into the reservoir and the syringe needle is withdrawn. The membrane self-seals to prevent any insulin from leaking out into body tissues.

These membranes have also been used in the ventilator field for administering drugs to a patient. In U.S. Pat. No, 5,181,508 a connector for connection between a respirator and a patient. The connector has a membrane through which drugs can be administered.

In a corresponding manner, an anaesthetic liquid can be injected into the respirator's gas flow pathways in order to dispense the anaesthetic liquid for inspiration. The membrane is advantageously arranged near the gas flow generator for maximal vaporization/atomization of the anaesthetic liquid before it reach the lungs.

The portable anaesthetic machine can have a closed breathing system, whereby the membrane can be arranged, in principle, anywhere in the gas flow pathways.

To increase usefulness, the portable anaesthetic machine can be devised with the capability of delivering an additive gas into the gas flow pathways. The additive gas can be oxygen or nitrous oxide. A gas analyzer for analyzing the gas in the gas flow pathways can be integrated into the respirator.

The second of the above objects is achieved in a portable anaesthetic emergency kit formed by a portable anaesthetic machine according to the invention described above augmented with a dispensing system to permit the dispensing of liquid anaesthetic.

The dispensing system can be a syringe, pre-filled with a specific amount of an anaesthetic, or even a syringe and a number of different bottled anaesthetics. The choice of the dispensing system depends on the intended placement of the portable anaesthetic machine. The former version is preferable for certain emergency uses.

DESCRIPTION OF THE PREFERRED EMBODIMENTS

Figure 1:
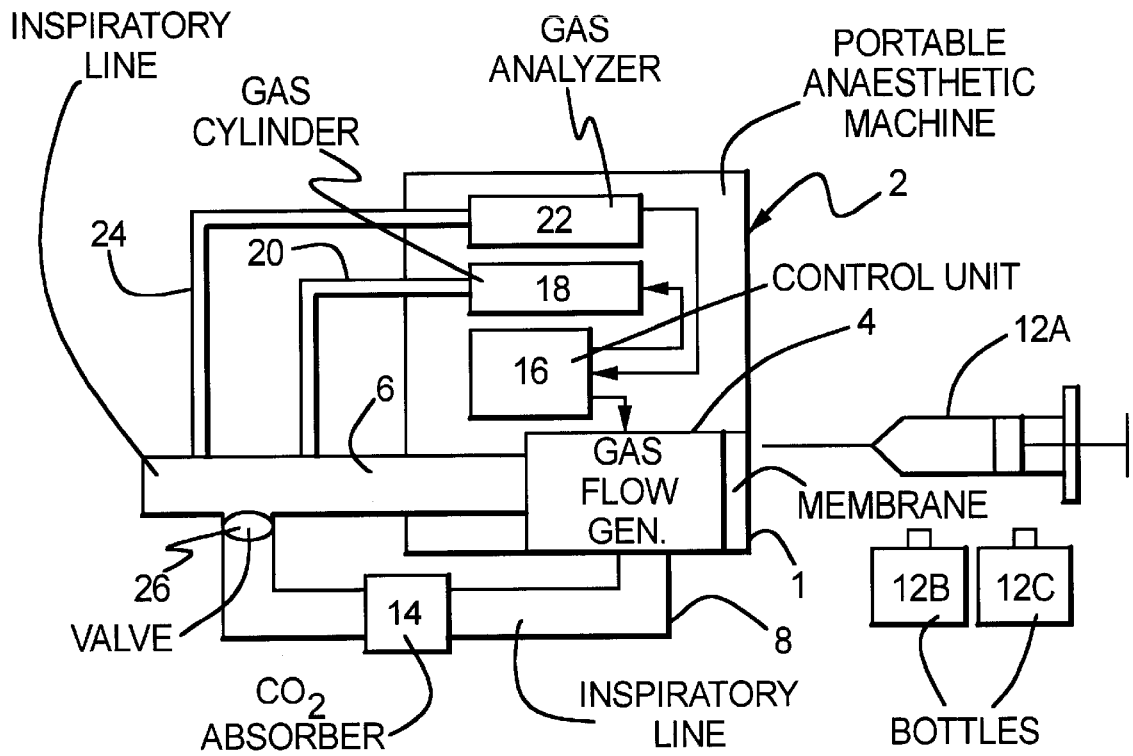
FIG. 1 shows a first embodiment of a portable anaesthetic machine and a dispensing system according to the invention.

The portable anaesthetic emergency kit in FIG. 1 includes a portable anaesthetic machine 2 with a gas flow generator 4. The gas flow generator 4 can be a turbine, fan, pump or similar generator in order to generate a specific pressure for and flow of ambient air (the air intake is not shown in FIG. 1). The breathing gas is sent from the gas flow generator 4 to an inspiratory line 6 for carrying breathing gas to a patient (not shown) Gas expired by the patient is returned to the gas flow generator 4 via an expiratory line 8.

A membrane 10, through which a liquid anaesthetic is injected with a syringe 12A (or some other suitable dispenser) is arranged at the gas flow generator 4. When the liquid anaesthetic is injected into the gas flow generator 4, it vaporizes and is carried with breathing gas to the patient. The liquid anaesthetic is contained in bottles 12B, 12C from which the user of the portable anaesthetic equipment can fill the syringe 12A with an appropriate anaesthetic and dispense it through the membrane 10. Since the gas flow pathways formed by the gas flow generator 4, the inspiratory line 6 and the expiratory line 8, are a closed system, safe and accurate dispensing of anaesthetic injected into the flow pathways is achieved. A carbon dioxide absorber 14 is located in the expiratory line 8 to absorb a sufficiently large part of the expired carbon dioxide and keep excessive concentrations of carbon dioxide from reaching the patient.

The anaesthetic machine 2 is controlled by a control unit 16 that can receive reference values from a user interface (not shown) for setting respiratory parameters. The control unit 16 mainly controls the gas flow generator 4 and also controls the dispensing of an additive gas from a gas cylinder 18 into the inspiratory line 6 via a dispensing line 20. The additive gas an be oxygen or a mixture of oxygen and nitrous oxide. The control unit 16 can control the respirator 2 on the basis of the gas concentrations measured by a gas analyzer 22. The gas analyzer 22 can collect gas by a gas analyzer 22. The gas analyzer 22 can collect gas samples for analysis via a gas sampling line 24.

If the gas analyzer 22 is an analyzer which pumps relatively large amounts of gas, gas samples should be returned to the breathing gas in the circle system. The gas samples can be appropriately returned to the gas flow generator 4. If the gas analyzer 22 requires relatively small volumes (compared to the total volume in the closed system), these volumes can instead be discharged into atmosphere. However, the advantage of re-using gas samples is that discharge of anaesthetic into atmosphere is minimized. This is particularly important when the respirator is used in environments with limited air change rates, e.g. in aircraft. There is also minimum impact on the operator.

Since the respirator 2 in FIG. 1 is devised so the expiratory line 8 is connected to the inspiratory line 6, an expiratory valve 26 is arranged at the connection point.

Figure 2:
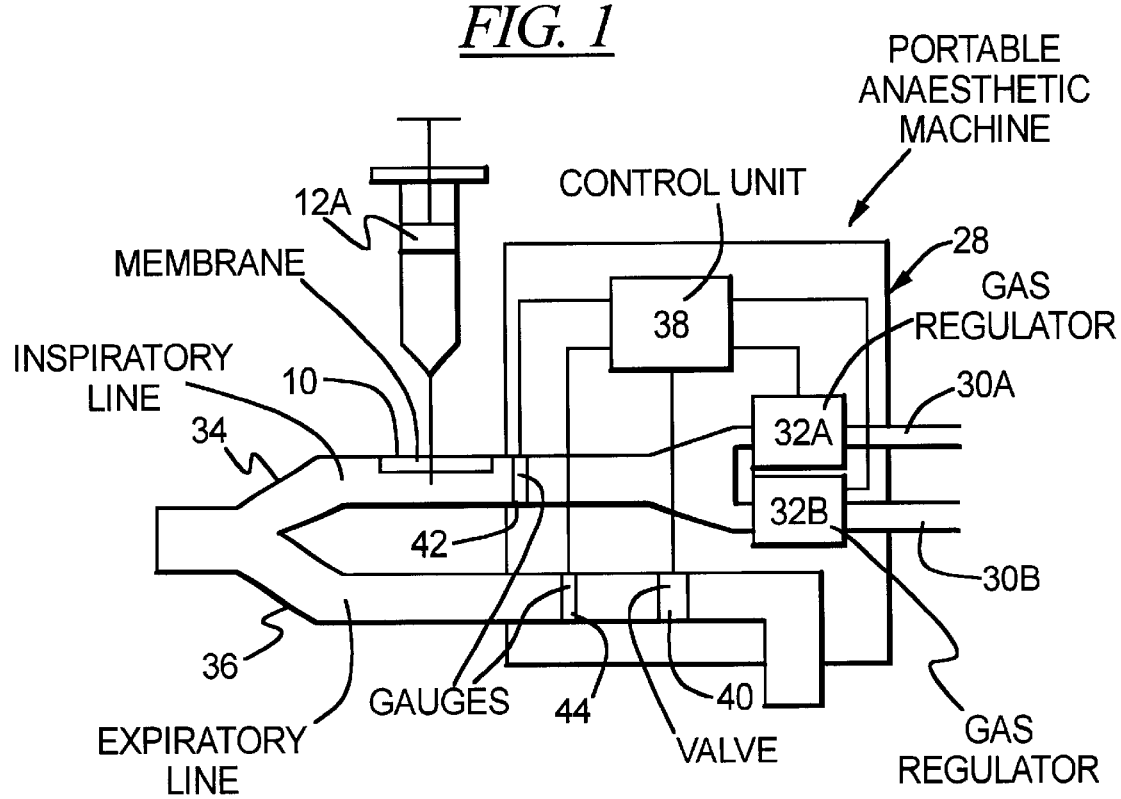
FIG. 2 shows a second embodiment of a portable anaesthetic machine and a dispensing system according to the invention.

Another embodiment is shown in FIG. 2. Components or devices which are identical to those in the previous embodiment have the same designations. The anaesthetic machine 28 includes a first gas connector 30A and a second gas connector 30B for connection of gas under pressure to the anaesthetic machine 28. Each gas is dispensed with an exact flow and pressure in a first gas regulator 32A and a second gas regulator 32B. The gases are mixed into a breathing gas and carried in an inspiratory line 34 to a patient (not shown) for inspiration. A membrane 10 is also arranged in the inspiratory line 34 into which an anaesthetic liquid is injected by a syringe 12A or the like.

Expired gas is returned in an expiratory line 36 to the anaesthetic machine 28 for transport to an exhaust unit.

A control unit 38 controls all the functions in the anaesthetic machine 28, especially the gas regulators 32A, 32B and an expiratory valve 40. The gauges 42, 44 for flow and/or pressure supply the control unit 38 with information on current values.

Combinations of the illustrated embodiments are possible where appropriate. For example, the membrane 10 can be located in the mixing chamber after the gas regulators 32A, 32B in the anaesthetic machine 28 in FIG. 2. A gas analyzer can also be used in the respirator 28. Recirculation in a closed system can also be used with the anaesthetic machine 28. It should then be combined with a carbon dioxide absorber.

Although modifications and changes may be suggested by those skilled in the art, it is the intention of the inventor to embody within the patent warranted hereon all changes and modifications as reasonably and properly come within the scope of his contribution to the art.

I claim as my invention:

1. A portable anesthetic machine comprising:

a gas flow generator which generates a flow of gas having a pressure and a flow rate, at least one of said pressure and flow rate being adjustable;

an inspiratory line connected to said gas flow generator;

a separate expiratory line communicating with said inspiratory line, said inspiratory line, said expiratory line and said gas flow generator comprising a gas flow pathway; and a membrane disposed in said gas flow pathway and being exteriorly accessible, said membrane comprising self-sealing material through which a predetermined amount of a liquid anesthetic can be dispensed into said gas flow pathway a repeated number of times.

2. A portable anesthetic machine as claimed in claim 1 wherein said membrane is disposed substantially adjacent to said gas flow generator.

3. A portable anesthetic machine as claimed in claim 1 wherein said expiratory line is connected to said gas flow generator and wherein said gas flow pathway comprises a closed system, and further comprising a carbon dioxide absorber disposed in said gas flow pathway.

4. A portable anesthetic machine as claimed in claim 1 wherein said gas flow generator comprises a turbine.

5. A portable anesthetic machine as claimed in claim 1 wherein said gas flow generator comprises a fan.

6. A portable anesthetic machine as claimed in claim 1 further comprising a gas cylinder containing an additive gas in communication with said gas flow pathway for dispensing said additive gas into said gas flow pathway.

7. A portable anesthetic machine as claimed in claim 6 wherein said gas cylinder contains a gas selected from the group consisting of oxygen and nitrous oxide.

8. A portable anesthetic machine as claimed in claim 1 further comprising a gas analyzer, communicating with said gas flow pathway, for analyzing at least one component gas in said gas flow pathway.

9. A portable anesthetic emergency kit comprising:

a gas flow generator which generates a flow of gas having a pressure and a flow rate, at least one of said pressure and flow rate being adjustable;

an inspiratory line connected to said gas flow generator;

a separate expiratory line communicating with said inspiratory line, said inspiratory line, said expiratory line and said gas flow generator comprising a gas flow pathway;

a membrane disposed in said gas flow pathway and being exteriorly accessible, said membrane comprising self-sealing material through which a predetermined amount of a liquid anesthetic can be dispensed into said gas flow pathway a repeated number of times; and dispensing means adapted to contain said liquid anesthetic which can be brought into communication with said membrane for dispensing said predetermined amount of said liquid anesthetic into said gas flow pathway through said membrane.

10. A portable anesthetic emergency kit as claimed in claim 9 wherein said dispensing means comprises at least one bottle containing said liquid anesthetic and a syringe for drawing said liquid anesthetic from said bottle and for puncturing said membrane to dispense said predetermined amount of said liquid anesthetic into said gas flow pathway.

11. A portable anesthetic emergency kit as claimed in claim 10 wherein said at least one bottle contains a liquid anesthetic selected from the group consisting of halothane, Isoflurane and Enflurane.

12. A portable anesthetic emergency kit as claimed in claim 9 wherein said dispensing means comprises at least one syringe filled with a predetermined dose of said liquid anesthetic.

13. A portable anesthetic emergency kit as claimed in claim 12 wherein said syringe contains a liquid anesthetic selected from the group consisting of halothane, Isoflurane, and Enflurane.

* * * * *